United States Patent [19]

Meybeck et al.

[11] Patent Number: 5,609,873
[45] Date of Patent: Mar. 11, 1997

[54] USE OF AN ECDYSTEROID FOR THE PREPARATION OF COSMETIC OR DERMATOLOGICAL COMPOSITIONS INTENDED, IN PARTICULAR, FOR STRENGTHENING THE WATER BARRIER FUNCTION OF THE SKIN OR FOR THE PREPARATION OF A SKIN CELL CULTURE MEDIUM, AS WELL AS TO THE COMPOSITIONS

[75] Inventors: Alain Meybeck; Frédéric Bonte, both of Courbevoie; Gérard Redziniak, Saint Cyr En Val, all of France

[73] Assignee: LVMH Recherche, Nanterre, France

[21] Appl. No.: 393,009

[22] PCT Filed: Aug. 20, 1993

[86] PCT No.: PCT/FR93/00819

§ 371 Date: Apr. 27, 1995

§ 102(e) Date: Apr. 27, 1995

[87] PCT Pub. No.: WO94/04132

PCT Pub. Date: Mar. 3, 1994

[30] Foreign Application Priority Data

Aug. 25, 1992 [FR] France .................................. 92 10267

[51] Int. Cl.$^6$ .......................... A61K 35/78; A61K 9/127; A61K 35/12; A61K 35/64
[52] U.S. Cl. ...................... 424/195.1; 424/450; 424/520; 424/538; 514/169; 514/863; 514/873
[58] Field of Search ............................... 424/195.1, 450, 424/520, 538; 514/169, 863, 873

[56] References Cited

U.S. PATENT DOCUMENTS

| | | | |
|---|---|---|---|
| 3,354,152 | 11/1967 | Edwards et al. | 540/61 |
| 3,354,154 | 11/1967 | Edwards et al. | 540/61 |
| 3,378,549 | 4/1968 | Edwards et al. | 540/61 |
| 3,440,241 | 4/1969 | Siddall | 540/115 |
| 3,455,905 | 7/1969 | Edwards et al. | 540/61 |
| 3,527,777 | 9/1970 | Jizba et al. | 552/541 |
| 4,508,703 | 4/1985 | Redziniak et al. | 428/38 |
| 4,621,023 | 11/1986 | Redziniak et al. | 428/482.2 |

FOREIGN PATENT DOCUMENTS

| | | | |
|---|---|---|---|
| 1494371 | 8/1966 | France . | |
| 1498237 | 11/1966 | France . | |
| 1525385 | 4/1967 | France . | |
| 1524924 | 5/1967 | France . | |
| 2201991 | 1/1972 | Germany | C07J 9/00 |
| 2834703 | 8/1978 | Germany | C07J 9/00 |
| 29390 | 1/1903 | Hungary . | |
| 46-14665 | 4/1971 | Japan . | |
| 59-10600 | 1/1984 | Japan | C07J 9/00 |
| 63-2928 | 1/1988 | Japan | C07J 9/00 |
| 478565 | 9/1969 | Switzerland | A61K 7/00 |
| 924051 | 4/1982 | U.S.S.R. | C07G 15/00 |
| 1146050 | 3/1985 | U.S.S.R. | A61K 35/78 |
| 9003778 | 4/1990 | WIPO | A61K 7/00 |

OTHER PUBLICATIONS

"Insect Growth Hormones and Their Effects On Some Plants", Ciencia e Cultura, 1980, vo. 32, No. 10, G. M. Felippe, pp. 1384–1390.
"Molecular Biology Of Keratinocyte Differentiation", Journal Environment Health Perspective, vol. 30, 1989, pp. 109–116.
A. Butenandt et al., Z. Naturforsch. B., 9, p. 389, 1954.
"La Culture De Cellules Animales", Sylvie Guichard–Balestini, Journal Biofuture, Supplement No. 56, Apr. 1987, pp. 2–14.
"Development Of A Hollow–Fiber System For Large–Scale Culture Of Mammalian Cells", K. Ku et al., Biotechnology and Bioengineering vol. XXIII, pp. 79–95, 1981.
"Large–Scale Cell Culture In Biotechnology", W. R. Arathoon et al., Science, pp. 1390–1395, vol. 232, 1986.
"Enjeux Et Problematiques", A. Berkaloff et al., CNRS Publication, Biologie 1990 Horticultural Abs. OC051–01546, 1980, vol. 16, No. 2, pp. 193–198.
Bio/Technology, vol. 61 Jan. 1988, pp. 41–44.
"A New Method For Studying Epidermalization", B. Coulomb et al., British Journal of Dermatology, 1986, vol. 114, pp. 91–101.
"Les Peaux Artificelles Vivante", La Recherche, 1987, vol. 185, pp. 149–159.
Merck Index, 10th Edition, 1983, p. 505, No. 3470.
Chemical Abstracts, vol. 111, No. 26 Dec. 25, 1989, Columbus, Ohio, U.S., Abstract No. 239323 (CN,A,86 106 791).
Chemical Abstracts, vol. 102, No. 15, Apr. 15, 1985, Columbus, Ohio, U.S., Abstract No. 128363 (SU,A, 1 130 605).

*Primary Examiner*—John W. Rollins
*Attorney, Agent, or Firm*—Lowe, Price, LeBlanc & Becker

[57] ABSTRACT

The invention relates to a cosmetic or dermatological composition, as well as a cell culture medium. This composition and this medium contain an ecdysteroid, an ecdysteroid derivative or a plant or animal extract containing it. This composition is aimed notably to give to skin a smoother and softer appearance, to strengthen the water barrier function of skin, and to strengthen the cohesion of the cells of the epidermis. This composition may also be used for improving the hair appearance. The cell medium may be used advantageously for the mass culture of keratinocytes.

15 Claims, No Drawings

USE OF AN ECDYSTEROID FOR THE PREPARATION OF COSMETIC OR DERMATOLOGICAL COMPOSITIONS INTENDED, IN PARTICULAR, FOR STRENGTHENING THE WATER BARRIER FUNCTION OF THE SKIN OR FOR THE PREPARATION OF A SKIN CELL CULTURE MEDIUM, AS WELL AS TO THE COMPOSITIONS

The present invention relates essentially to the use of an ecdysteroid for the preparation of cosmetic or dermatological compositions intended, in particular, for strengthening the water barrier function of the skin, or for the preparation of a cell culture medium, as well as to the compositions thereby obtained.

The ecdysteroids are a group of 2,3,14-trihydroxy-$\Delta$-7-6-ketosteroids. There may be mentioned $\alpha$-ecdysone or ($2\beta,3\beta,14\alpha,22[R],25$-pentahydroxy-7-cholesten-6-one); 2-deoxyecdysone or ($3\beta,14\beta,22[R],25$-tetrahydroxy-$5\beta$-7-cholesten-6-one); ecdysterone or $\beta$-ecdysone or $2\beta,3\beta,14\alpha$, $20\beta,22,25$-hexahydroxy-7-cholesten-6-one; $\beta$-ecdysone 22-acetate or 20-hydroxyecdysone 22-acetate or $2\beta,3\beta,14$, $20,22[R],25$-hexahydroxy-7-cholesten-6-one 22-acetate; 5-hydroxyecdysterone or $2\beta,3\beta,5\alpha,14,20,22[R],25$-heptahydroxy-$5\beta$-7-cholesten-6-one; and 2-deoxy-$\beta$-ecdysone or $3\beta,14,20,22[R],25$-pentanydroxy-$5\beta$-7-cholesten-6-one. The ecdysteroids, and especially ecdysterone (in some cases referred to as $\beta$-ecdysone or alternatively crustecdysone), are well known in the literature and mentioned in the Merck Index, 10th Edition, 1983, page 505, No. 3470.

Ecdysteroids, and especially ecdysterone, are known to play an important part both in the animal kingdom, in insects, and in the plant kingdom. In insects, these hormones play a key part in growth and reproduction. Ecdysterone participates especially in the different metamorphoses occurring up to the formation of the adult insect (see CNRS publication: Biologie 1990, "Enjeux et Problématiques" by A. Berkaloff et al.)

In plants, the activity of these substances has not been completely elucidated. They seem to affect flowering (CIENCIA e Cultura (1980), volume 32, No. 10, pages 1384–1390).

It has now been discovered that ecdysteroids, and especially ecdysterone and its acylated, in particular acetylated, derivatives, regulate keratinocyte differentiation.

This differentiation manifests itself especially, at epidermal level, in a greater cellular cohesion, in a regulation of keratinocyte transformation into corneocytes through loss of the nucleus and increase in cellular cornification, and in an increase in the number of layers of corneocytes forming the cornified layer, there phenomena collectively contributing to give the skin a smoother and softer appearance, to strengthen the protective function of the skin with respect to the external environment and to strengthen the water barrier preventing excessive water loss through the epidermis; and, at hair follicle level, to regulate or even increase the synthesis by keratinocytes of keratin, the main constituent of the pilar shaft of each individual hair.

A person skilled in the art may refer in this connection to the paper by Eckert and Rorke published in the Journal Environment Health Perspective, volume 30, (1989), page 109–116.

Thus, the main object of the present invention is to solve the technical problem that consists in providing an approach enabling keratinocyte differentiation to be regulated or promoted and which is, as a result, intended especially for treating skin disorders accompanied by a disturbance of keratinocyte differentiation, such as psoriasis, for restoring, preserving and/or strengthening the protective function of the epidermis, in particular through improvement or strengthening of the cornified layer and the water barrier function, thus leading to a hydrating effect, especially by preventing excessive water loss through the epidermis, en advantageous application of which is the treatment of ichthyotic skins as well as the treatment of psoriatic skins, and for improving the quality of hair, thus making the appearance of the hair more attractive.

The main object of the present invention is also to solve the technical problem that consists in providing an approach that enables the differentiation of skin cells, in particular keratinocytes, to be promoted, accelerated and improved during their culture in a culture medium.

The present invention solves these technical problems for the first time satisfactorily and in a manner which can be applied on an industrial scale for the preparation of cosmetic or dermatological compositions, or for the preparation of culture media, in particular media used in bulk culture of skin cells, as well as for this culturing.

Thus, according to a first aspect, the present invention relates to the use of at least one ecdysteroid or at least one ecdysteroid derivative or at least one plant or animal extract containing the said ecdysteroid or said ecdysteroid derivative, for the preparation of a cosmetic or dermatological composition intended for treating skin disorders accompanied by disturbances of keratinocyte differentiation, such as psoriasis, for restoring, preserving and/or strengthening the protective function of the skin, in particular through improvement or strengthening of the cornified layer and the water barrier function, as well as the cohesion of the cells of the epidermis, or alternatively for improving the quality of hair in terms of its constitution; or for the preparation of a cell or tissue culture medium, in particular for the bulk culture of skin cells, especially keratinocytes.

According to another particular embodiment, a combination of several ecdysteroids or ecdysteroid derivatives, or alternatively a combination of at least one ecdysteroid and of a plant or animal extract containing same, is used.

According to a particular embodiment, the abovementioned ecdysteroid is ecdysterone, or an ecdysterone derivative, in particular an acylated, hydroxylated or deoxy derivative thereof.

According to a preferred variant of implementation, the abovementioned acylated derivative is an ecdysterone mono- or multiacetate.

According to an especially advantageous mode of the invention, the ecdysterone derivative is chosen from the group consisting of beta-ecdysone 2-acetate, beta-ecdysone 3-acetate, beta-ecdysone 2,3-diacetate, beta-ecdysone 2,3,22-triacetate, beta-ecdysone 2,3,22,25-tetraacetate, 5-hydroxyecdysterone and 2-deoxyecdysterone.

According to another special feature of the extract invention, the abovementioned plant or animal containing the ecdysteroid, preferably ecdysterone is an extract of *Achyranthes bidentata, Paris axialis, Paris fargesii, Paris dunniana, Paris vietnamensis, Paris polyphylla, Polypodium vulgare, Cyanotis arachnoidea, Ajuga decumbens, Pfaffia paniculata, Pfaffia iresinoides, Vitex glabrata, Achyranthes aspera, Sesuvium portulacastrum, Serratula sogdiana, Rhaponticum integrifolium, Rhaponticum (or Leuzea) carthamoides, Silene tatarica, Silene otites, Silene scabrifolia, Silene nutans, Silene brahuica, Silene traemixta, Silene dioca, Lychnis flos-cuculi, Ajuga iva, Serratula tinctoria, Cyathula officinalis, Cyathula capitata* or *Bombyx mori.*

According to an especially advantageous embodiment, the preferred plant extracts are the extracts of *Polypodium vulgare, Ajuga decumbens, Cyanotis arachnoidea, Achyranthes bidentata* and *Rhaponticum (or Leuzea) carthamoides.*

According to another advantageous variant of implementation, a combination consisting of ecdysterone and at least one of its mono- or multiacetates, especially the 2- or 3-acetate, or a plant extract containing such a combination, is used. It has, in effect, been observed that acetate derivatives of ecdysteroid in combination with ecdysterone strengthen the abovementioned activities of the invention. This activity is strengthened further with additional combination with ajugasterone C, optionally in its 2- or 3-monoacetate form.

According to another special feature of the invention, the ecdysteroid or its derivative, or the plant or animal extract containing same, may be at least partially incorporated in liposomes.

It should be noted that the expression "at least partially incorporated in liposomes" is understood to mean that the ecdysteroid or its derivative, or the plant or animal extract containing same, is combined with liposomes irrespective of the form of this combination. In other words, in the context of the invention, the ecdysteroid or its derivatives or the plant or animal extract containing same may be totally encapsulated or partially encapsulated, or be on the outside simply in the presence of liposomes.

The preparation of liposomes at least partially containing at least one ecdysteroid according to the invention may be carried out according to one of the known processes for incorporating active substances, in particular steroids, in liposomes.

According to a preferred embodiment, according to the present invention, a process of atomization of the constituents of the lipid phase is used, enabling a lipid powder to be obtained which is readily dispersible in an aqueous solution to form liposomes, for example according to the process described in the document U.S. Pat. No. 4,508,703. The liposome suspension thereby obtained may be homogenized by means of ultrasound or, in the case of a bulk production, by means of a homogenization under pressure, according to the process described in U.S. Pat. No. 4,621,023.

According to a preferred embodiment of the invention, the ecdysteroid or its derivative or a plant or animal extract containing same is incorporated in the lipid phase of liposomes. Thus, the ecdysteroid or its derivative, or an extract containing it, is dissolved with the constituents of the lipid phase, before atomization, in an organic solution containing at least one amphiphilic lipid, such as soya bean lecithin, and optionally a lipophilic hydrophobic compound such as cholesterol or β-sitosterol. Preferably, the solvent is chosen from dichloromethane, chloroform or methanol, or one of the mixtures thereof.

The organic solution can advantageously contain an antioxidant such as α-tocopherol.

The lipid powder obtained is dispersed in a suitable aqueous medium, for example a PBS buffer solution, a glucose solution or a sodium chloride solution. A liposome suspension is thereby obtained.

According to an advantageous embodiment, most especially in the case of a liposome composition, after the composition obtained has, where appropriate, been homogenized, the liposome compositions are gelled by mixing with a gel, such as a vinyl polymer gel, especially marketed under the tradename Carbopol® 940. This gelling procedure is also described U.S. Pat. No. 4,508,703, especially in the examples.

According to an advantageous embodiment of the invention, the ecdysteroid concentration is between 0.001 and 30% by weight, and preferably between 0.01 and 10% by weight, of the lipid phase of the said liposomes.

According to another advantageous embodiment of the invention, the ecdysteroid or its derivative or a plant or animal extract containing same is at least partially included in cyclodextrin. For this purpose, a procedure well known to a person skilled in the art may be used. For example, cyclodextrin is solubilized in an aqueous buffer, for example of the PBS type. An ecdysteroid or its derivative or a plant or animal extract containing same is then added in an equimolecular amount with stirring at room temperature. The stirring is continued until a clear solution is obtained. This solution is then used for the preparation of a cosmetic or dermatological composition according to the invention. The procedure is the same in the case of a combination as described above. As a result of this inclusion in cyclodextrin, the activity of the ecdysteroid or its derivative, or of a plant or animal extract containing same, is unexpectedly improved considerably. The proportion of cyclodextrin and of ecdysteroid or its derivative or a plant or animal extract containing same in the solubilization solution can vary within wide limits. Preferably, this concentration will be, for cyclodextrin, between 0.1% and 5% by weight, and, for the ecdysteroid, between 0.01% and 2% by weight.

The ecdysteroids or their derivatives, preferably ecdysterone or its derivatives, are obtained in isolated form, or in the form of an extract from all available natural sources, or alternatively by a process of chemical synthesis. The main natural sources of ecdysteroids are insects, and most especially a large number of plants, such as the plants mentioned above. Also, a number of synthesis processes have been developed.

Extraction from insects

The amount of ecdysteroid, especially α- or β-ecdysone, present in insects is extremely small. In the Bombyx mori moth, it is, for example, $5 \times 10^{-6}$% by weight of insect (see A. Butenandt et al., Z. Naturforsch. B., 9, 389, (1954)).

Hence the extraction of ecdysteroid from insects cannot generally constitute an industrial production process.

However, in the document Hunger-Ricci CH-A-478,565, the extraction of ecdysterone from nymphs or from chrysalids is described, it being intended for the preparation of cosmetic compositions.

Extraction from plants

The concentration of ecdysteroids, especially of ecdysterones, varies from one variety to another. For example, the ecdysterone concentration is 0.025% in Achyranthes aspera seeds and 0.35% in the Sesuvium portulacastrum plant. The percentages are percentages by weight of dry matter.

Among the plants which may be used for the extraction of ecdysteroids, especially of ecdysterone, there may be mentioned: *Serratula sogdiana* and *Rhaponticum integrifolium*, which have the advantage of being able to be cultivated (see Horticultural Abs. OC051-01546, referring to Rastitel'nye Resursy, (1980), volume 16, No. 2, pages 193–198 (in Russian)).

Extractions from the following may also be mentioned:

*Serratula tinctoria* (HUT-029,390);

*Serratula inermis* (SU-1,146,050);

*Achyranthes fauriei*, (FR-1,525,385);

Cyathula (FR-1,525,385);

*Polypodium vulgaree* (U.S. Pat. No. 3,527,777);

*Cyanotis arachnoidea* (C. A. 89-176,352, referring to the publication by Nien Schui Lin et al. Acta Chimica Sinica, 1978, volume 36, No. 2, pages 137–141);

*Ajuga decumbens* (JP-46-014,665);

*Pfaffia iresinoides* (Derwent 88-045806 or JP-63-002, 928);

*Pfaffia paniculata* (Derwent 84-052423 or JP-59-010,600);

Kaladana seed (DE-2,201,991);

*Ipomea petaloidea* (DE-2,834,703);

Silenes (HUT 029,390 and SU 924,051).

These sources of ecdysteroids are given without implied limitation and are not exhaustive.

Besides ecdysterone, some extracts can also contain acetylated derivatives (C.A. 89-176352).

It is also possible to obtain the ecdysteroids according to the invention by chemical synthesis (see, for example, U.S. Pat. No. 3,354,152, U.S. Pat. No. 3,354,154, U.S. Pat. No. 3,378,549, U.S. Pat. No. 3,455,905, FR-1,494,371; U.S. Pat. No. 3,440,241; FR-1,524,924; U.S. Pat. No. 3,378,549 and FR-A-1,498,237).

An example of a general process for the extraction of ecdysteroid, preferably ecdysterone, from plants is described in Chem. Pharm. Bull. (1969) 17 (2) 340–2 by S. Imai et al.

The fresh plant is macerated in 5 times its weight of methanol and the mixture is homogenized and filtered. This operation is repeated once more. The extracts are concentrated, and water is added to form a 30% methanol/water solution.

This solution is extracted with hexane. The 30% methanol fraction is concentrated again and extracted with ethyl acetate. The aqueous fraction is extracted with n-butanol. The butanol extract is then concentrated by evaporation and thereafter treated by chromatography on silica gel with a chloroform/methanol mixture. After recrystallization in an ethanol/ethyl acetate mixture., ecdysterone is thereby obtained in the form of colourless needles.

It is also possible to obtain monoacetylated derivatives of ecdysteroids by chemical methods well known to a person skilled in the art. For example, the ecdysteroid is brought into connect with a 1:5 by weight mixture of acetic acid and pyridine at room temperature. Reaction is generally allowed to take place for a period of 30 min to 1 h. The reaction is then stopped by adding methanol. A mixture of different monoacetates of the ecdysteroid is thereby obtained, which products may then be separated conventionally by chromatography. By this process, it is, for example, possible to prepare ecdysterone monoacetates at positions 2, 3, 22 and 25, respectively.

Moreover, a number of ecdysteroids are commercially available. For example ecdysterone, 5-hydroxyecdysterone, 2-deoxyecdysterone, ecdysterone 22-acetate, α-ecdysone and 2-deoxy-α-ecdysone are available from SIGMA under the references SIGMA H 5142, SIGMA P 9531, SIGMA D 7775, SIGMA H 5267, SIGMA E 9004 and SIGMA D 7900.

The compositions according to the invention described above, containing an ecdysteroid, preferably ecdysterone, or its derivatives, optionally in a form at least partially incorporated in hydrated lamellar lipid phases or in liposomes, can take different forms which are usable in cosmetics or in dermatology. For example, these compositions can be gels, creams, milks or lotions.

These compositions, applied to the areas of the skin to be treated, have the effect of regulating keratinocyte differentiation, thereby promoting the formation or restoration of a good quality epidermis, in particular in respect of the cornified layer, especially as regards its composition and its structural organization. This enables the epidermis, on the one hand, in particular through a strengthened cellular cohesion, to possess properties of optimal protection with respect to surrounding environments, and on the other hand to treat disorders of the epidermis accompanied by a disturbance of keratinocyte differentiation.

Thus, the compositions according to the invention make it possible, in particular, to restore, preserve and strengthen the protective skin barrier function of the epidermis, especially the water barrier function, and thereby to obtain, in particular, a hydrating effect by preventing excessive water loss through the epidermis. The compositions according to the invention may hence be advantageously used for the treatment of dry skins, irrespective of the degree of dryness, including ichthyotic skins, and the treatment of psoriatic skins.

According to a second aspect, the invention also relates to a cosmetic or dermatological composition intended for treating skin disorders accompanied by disturbances of keratinocyte differentiation, such as psoriasis, for restoring, preserving and/or strengthening the protective function of the skin, in particular the strengthening or improvement of the cornified layer and the water barrier function, as well as the cohesion of the cells of the epidermis, or alternatively for improving the quality of hair in terms of its constitution, characterized in that it contains as active agent an ecdysteroid or an ecdysteroid derivative, or a plant or animal extract containing the said ecdysteroid or said ecdysteroid derivative, as defined above.

According to another particular embodiment, the cosmetic or dermatological composition according to the invention displays a hydrating power, in particular by preventing excessive water loss through the epidermis, and can be intended for the treatment of dry skins, in particular ichthyotic skins.

According to another particular embodiment, the cosmetic or dermatological composition according to the invention enables normal keratinocyte differentiation to be restored, and can be intended for the treatment of psoriatic skins.

In this context, the ecdysteroid or ecdysteroid derivative is usually incorporated in a cosmetically or dermatologically acceptable excipient. In addition, the ecdysteroid or ecdysteroid derivative mentioned above, or a plant extract containing same, may be incorporated in hydrated lamellar lipid phases or liposomes, as has been described for the first aspect above.

According to a third aspect, the invention also relates to a cell or tissue culture medium, in particular for the bulk culture of skin cells, characterized in that it comprises an amount which is effective for promoting, accelerating or improving the differentiation of skin cells, especially keratinocytes, of at least one ecdysteroid or of at least one ecdysteroid derivative, or of at least one plant or animal extract containing same.

According to a fourth aspect, the invention also relates to a process for promoting, accelerating or improving the differentiation of skin cells, especially keratinocytes, in particular in the context of a bulk culture of skin cells, for the production of artificial skin or for the preparation of models of reconstituted skin, characterized in that a culture medium as defined in the context of a use above, or in the description which follows taken as a whole, is used.

This process according to the invention, termed a cell differentiation process, is, in particular, of great industrial importance. There may be mentioned, for example:

the production of biochemical mediators by bulk culture treatment of keratinocytes in bioreactors;

the preparation of artificial skin for the purpose of carrying out skin grafts, the process of the invention being especially advantageous in the case of autografts of third-degree burns victims, as a result of the gain in time it achieves in the preparation of an artificial skin.

In particular, the acceleration and improvement of keratinocyte differentiation manifests itself in the faster formation of a good quality cornified layer;

the production of skin models comprising reconstituted skin, intended, for example, for evaluating the skin penetration or the toxicity of substances or compositions applied topically, when they are intended especially for a local treatment or for a systemic treatment (transdermic in particular).

According to a particular variant of implementation, this culture process will generally comprise the preparation of a culture medium for the growth of human keratinocytes comprising a DMEM (Gibco®) nutrient base medium, an epidermal growth factor ("EGF"), 10% of foetal calf serum, isoproterenol and/or forskolin, as well as hydrocortisone. In the context of the invention, this medium also comprises an ecdysteroid or an ecdysteroid derivative or a plant or animal extract containing same, as described in the above or following description, for example β-ecdysone or one of its derivatives, especially acetate, generally at a concentration of 0.01 to 0.5% by weight.

In this process, bulk culturing of skin cells is carried out by inoculating keratinocytes so as to immobilize them on supports such as hollow fibres, microbeads or microporous matrices, this being done using the above culture medium. It is possible to provide for a perfusion of the medium so as to have a supply which is sufficient for growth and differentiation even when the biomass is large.

The culture medium according to the invention can advantageously be used for the bulk culture of skin cells, especially keratinocytes, for the production of artificial skin or for the preparation of models of reconstituted skin.

In the context of the use in a culture medium, according to a particular variant of implementation, it is possible to use from 0.01 to 0.5% by weight of ecdysteroid, of ecdysteroid derivative or of plant extract containing same, relative to the total weight of the final culture medium.

Furthermore, according to an especially advantageous embodiment, a supplementary active principle, especially an active principle having a hydrating effect, such as hyaluronic acid, may be introduced into the cosmetic or dermatological composition.

According to yet another aspect, the present invention relates to a cosmetic treatment process for restoring, preserving and/or strengthening the protective function of the skin, including the water barrier function, for restoring, preserving and/or strengthening the cornified layer and for improving the quality of hair in terms of its constitution, characterized in that a cosmetically effective amount of a composition containing at least one ecdysteroid or at least one ecdysteroid derivative or at least one plant or animal extract containing same, especially at a concentration of between 0.0001 and 5%, and preferably between 0.01 and 1%, by weight relative to the total weight of the composition, is applied to relevant areas of the skin or scalp of a relevant person.

Preferably, in the different aspects above of the invention, the concentration by weight of ecdysteroid, of ecdysteroid derivatives or of a plant extract containing same in the final cosmetic or dermatological composition is between 0.0001 and 5%, and as a further preference between 0.01 and 1%, by weight relative to the total weight of the composition.

Other objects, features and advantages of the invention will become apparent in the light of the explanatory description which follows, done with reference to several examples of implementation of the invention which are given simply by way of illustration and which could hence in no way limit the scope of the invention.

In the examples, the percentages are given by weight except where otherwise stated.

EXAMPLE 1

Test of activity with respect to keratinocyte differentiation

For the present study, a skin sample taken during an operation of aesthetic surgery of the "lifting" type from the face of a 42-year-old woman is used.

On day D=−2, six Petri dishes are inoculated with $10^5$ keratinocyte cells, isolated from this sample, into a conventional culture medium for culturing keratinocytes which is well known to a person skilled in the art.

On day D=0 and on day D=7, the culture medium is renewed with an identical medium in three of the six dishes, which constitute untreated control dishes, and in the remaining three dishes which constitute the treated dishes, renewal is with an identical medium but in which 250 µg/ml of ecdysterone has been dissolved.

On day D=12, a cell count is carried out, as well as an inclusion of the cells in epoxy resin after fixing and staining the cellular structures with uranyl acetate.

Sectioning of each of the blocks of resin thereby obtained is carried out in the form of ultrathin sections, for example using a device known by the name of microtome, and which are observed in a transmission electron microscope.

Table I below records this observation for each of the three zones of the control culture on the one hand, and of the culture treated with ecdysterone on the other hand.

TABLE I

| | Control | Ecdysterone |
|---|---|---|
| Upper zone | Signs of degeneration No cornified envelope around the cells of the most differentiated upper cellular layers No keratohyalin granules | More substantial cornified layer Numerous corneocytes with a thick cornified envelope Differentiated desmosomes Keratohyalin granules Fewer organelles |
| Intermediate zone | A few tonofilaments Large intercellular spaces A few desmosomes | Keratin filaments Many tonofilaments Reduced intercellar spaces |
| Basal zone | A few hemidesmosomes | Cytokeratin filaments Numerous hemidesmosomes |

It is seen from Table I above that, with the use of ecdysterone, according to the present invention, a culture is obtained consisting of numerous layers of highly differentiated keratinocytes, thereby demonstrating in a highly significant manner the regulatory effect of an ecdysteroid such as ecdysterone on keratinocyte differentiation.

In addition, as a result of the effect of normalization of keratinocyte differentiation, the compositions according to the invention containing an ecdysteroid, as defined above, enable a good state of the epidermis of "normal" skin to be maintained, in particular by maintaining its suppleness and its functional role, especially its protective barrier role.

The compositions of the invention may thus be used advantageously for hydrating the skin, for preventing and treating dry skins displaying different degrees of dryness, including ichthyotic skins, or for treating psoriatic skins.

It should be noted, in effect, that the phenomenon of dry skins or of psoriasis is accompanied by a disorder of keratinocyte differentiation. In particular, psoriatic keratinocytes are poorly developed and immature, the number and size of the tonofilaments are altered, and some cells of the cornified layer still contain organelles or even a nucleus, showing that differentiation has not taken place correctly. Large intercellular spaces are also observed in the case of these complaints.

In the case of dry skins, especially ichthyosis, keratinocyte differentiation is imperfect, accompanied by malformation of the keratohyalin granules and desmosomes. The epidermis displays an abnormal keratinization, leading to a disturbance of the barrier, in particular water barrier, properties, and a loss of elasticity.

Various examples of industrially usable cosmetic or dermatological compositions are now given.

EXAMPLE 2

Dermatological composition for restoring the water barrier of the epidermis

| | |
|---|---|
| Ecdysterone | 0.5 g |
| Cremophor RH40 ® | 1 g |
| Carbomer 980 ® | 0.2 g |
| Triethanolamine | 0.18 g |
| PEG 6-32 stearate | 7 g |
| Cetyl alcohol | 2 g |
| Vegetable oils | 25 g |
| Perfumed aqueous excipient | q.s. 100 g |

The above components are mixed conventional manner to obtain a treatment emulsion applied morning and night while gently massaging the areas to be treated. This emulsion is used as a day and/or night cream.

EXAMPLE 3

Dermatological composition for treating psoriatic skins

| | |
|---|---|
| Ecdysterone-2-acetate | 0.3 g |
| Carbopol 980 ® 2% gel | 35 g |
| Perfumed aqueous excipient | q.s. 100 g |

The ecdysterone 2-acetate is introduced into the aqueous excipient to dissolve it, and the Carbopol gel is then added so as to obtain a gelled composition which is applied locally on the lesions for 6 weeks.

EXAMPLE 4

Cosmetic composition for maintaining a satisfactory state of hydration of the epidermis

| | |
|---|---|
| Ecdysterone | 0.18 g |
| α-Bisabolol | 0.1 g |
| Hyaluronic acid | 1 g |
| Urea | 3 g |
| Cosmetically acceptable excipient in the form of a body milk | q.s. 100 g |

The milk is applied to the areas to be treated, especially to the legs after depilation. This composition makes it possible, in particular, to strengthen the cutaneous water barrier function of the epidermis by improving epidermal intercellular cohesion. It thus enables the skin to retain a satisfactory state of hydration.

EXAMPLE 5

Liposomal cosmetic composition for re-equilibrating the desquamation of the cornified layer of the epidermis, and restoring smoothness to the epidermis

| | |
|---|---|
| Ecdysterone | 0.1 g |
| Soya bean lecithin | 2 g |
| β-Sitosterol | 0.2 g |
| Cosmetic cream oil-in-water type emulsion based on squalane | q.s. 100 g |

In a first step, an aqueous suspension of liposomes encapsulating ecdysterone in the lipid phase of the said liposomes is prepared. For this purpose, the procedure is as follows.

0.1 g of commercial ecdysterone, 2 g of soya bean lecithin and 0.2 g of β-sitosterol are dissolved in 50 ml of a 4:1 mixture of dichloromethane and methanol. This solution is evaporated under reduced pressure (approximately 200 mm of mercury) in a rotating round-bottomed flask brought to 45° C. The lipid film obtained is taken up with 25 ml of an aqueous solution of monopotassium phosphate at a concentration of 0.2 g/l and disodium phosphate at a concentration of 1.44 g/l, with stirring for 1 h.

Approximately 25 ml of a suspension of liposomes encapsulating ecdysterone are thereby obtained, which suspension is then subjected to a homogenization with ultrasound (15 min, 150 W, 4° C.).

In a second step, the liposome suspension obtained is incorporated in a conventional manner in the emulsified excipient to obtain the cream according to the invention.

The cream may be applied daily to the face in the case of rough skin or skin peeling off in scales.

This composition strengthens the cohesion of the cornified layer, and normalizes the detachment of dead cells, thereby giving them the appearance of a smoother epidermis.

EXAMPLE 6

Preparation of an extract of the plant *Rhaponticum carthamoides*

250 g of dry roots of the plant *Rhaponticum carthamoides* are reduced to powder and extracted for 2 h with 2.5 l of methanol at the boil under reflux.

After a meticulous filtration to remove any solid particle, the solvent is evaporated off until a dry product, designated "extract of the plant *Rhaponticum carthamoides* according to the invention", in the so-called dry state, is obtained.

This crude extract may be employed in the preparation of cosmetic and/or pharmaceutical formulations, as well as for the preparation of a culture medium.

EXAMPLE 7

Preparation of an extract of the plant *Achyranthes bidentata*

The procedure is as described in Example 6, except that dry roots of the plant *Achyranthes bidentata* are used.

The product obtained is designated "extract of the plant *Achyranthes bidentata* according to the invention", in the dry state.

This crude extract may be employed in the preparation of cosmetic and/or pharmaceutical formulations, as well as for the preparation of culture media.

EXAMPLE 8

Cosmetic composition containing a *Rhaponticum carthamoides* plant extract, intended for the preventive treatment of dry skins

| | |
|---|---|
| Rhaponticum carthamoides extract obtained in Example 6 | 0.5 g |
| Cream emulsion excipient of the oil-in-water type, q.s. | 100 g |

The *Rhaponticum carthamoides* extract is incorporated in a conventional manner in the cream emulsion excipient to obtain the cream according to the invention.

The cream may be applied daily to the parts of the body which it is desired to treat.

EXAMPLE 9

Cosmetic composition containing an *Achyranthes bidentata* plant extract, intended for the treatment of ichthyotic skins

| | |
|---|---|
| Glycerol | 3 g |
| Hyaluronic acid | 1 g |
| Achyranthes bidentata extract obtained in Example 7 | 0.2 g |
| Cream emulsion excipient of the oil-in-water type, q.s | 100 g |

The *Achyranthes bidentata* extract is incorporated in a conventional manner together with the glycerol and the hyaluronic acid in the cream emulsion excipient to obtain the cream according to the invention.

This cream is applied daily to the desired areas of the skin, until a much smoother skin is obtained by means of an action on the corneocytes, leading to a strengthening of their cornified envelope and to a better cohesion with one another.

EXAMPLE 10

Cosmetic composition for re-equilibrating the state of the skin, containing on ecdysteroid combination The following ecdysteroid combination is prepared beforehand:

approximately 85% of ecdysterone;

approximately 13% of a racemic mixture containing ecdysterone 2- and 3-monoacetate;

approximately 2% of ajugasterone C.

Ecdysterone is commercially available. Its 2- or 3-acetate derivatives may be prepared chemically according to a conventional controlled acetylation process, in the presence of an acetic acid/pyridine mixture, as has been described above. Ajugasterone C may be obtained by extraction from a plant, especially of the species Ajuga, for example according to the process described in the document JP 71-028038 from the plant *Ajuga decumbens*.

These products are solubilized in a 50% aqueous-alcoholic mixture. The solution is then evaporated to dryness to give the abovementioned combination in powder form.

This combination is then introduced into a cosmetically acceptable cream emulsion excipient of the oil-in-water type, for example in a sufficient amount to obtain a concentration of 0.05% of ecdysteroid relative to the total weight of the cosmetic composition thus prepared.

EXAMPLE 11

Cosmetic composition having a hydrating and regenerating effect containing a combination of ecdysteroid and cyclodextrin The ecdysteroids of the combination prepared in Example 10 are dispersed at a concentration of 1% in an aqueous solution containing 2.5% of cyclodextrin, with stirring until a clear solution is obtained. In this manner, the ecdysteroids are included in the cyclodextrin molecules. This solution of cyclodextrin including ecdysteroids is added to a cream emulsion excipient of the oil-in-water type in a sufficient amount to form an emulsion containing 0.1% by weight of ecdysteroid.

This composition may be applied daily to the desired areas of the skin to strengthen its state of hydration and obtain a much smoother skin.

EXAMPLE 12

Preparation of a culture medium and its use for the bulk culture of skin cells

For the preparation of this culture medium, as well as for its use for the bulk culture of skin cells, a person skilled in the art may refer, in particular, to the paper by Philip C. Familletti et al. in Biotechnology, volume 6, January 1988, pages 41 to 44, as well as to the references cited in this paper, especially Arathoon et al. in the Journal Science (1986), 232, pages 1390 et seq; and the paper by Ku, K. et al. in the journal Biotechnology Bioeng. (1981), 23, pages 79 et seq.

Thus, an optimal culture medium for the growth of human keratinocytes, comprising a DMEM (Gibco) nutrient base medium, growth factor EGF, 10% of foetal calf serum, isoproterenol and/or forskolin, as well as hydrocortisone, is prepared.

This medium will advantageously comprise 20-hydroxyecdysone or one of its derivatives at a concentration of 0.001 to 0.1%.

Bulk culturing of skin cells is carried out by inoculating keratinocytes so as to immobilize them on supports such as hollow fibres, microbeads or microporous matrices, this being done using the culture medium described above. Provision will be made for a perfusion with medium in a perfusion system of the type described by Sylvie Guichard-Balestrini in the Journal Biofutur, supplement No. 56, April 1987, pages 2 to 14, so as to have a supply which is sufficient for growth and differentiation even when the biomass is large.

At the end of culturing, the substances secreted by the keratinocyte cells, mainly containing lipids, sources of starting materials for the formulation of cosmetic or pharmaceutical compositions for topical application to the epidermis or scalp, are recovered.

By means of the product of the invention, it is possible to treat reconstituted skin cultures, especially cultures of keratinocytes or of epidermal cells cultured on a suitable support, such as a collagen-based support (containing or not containing fibroblasts), for example described in the document La Recherche, (1987), 185, p. 149–159 and in Br. J. Dermatol. 1986, 114, 91–101, or a support consisting of excised dermis.

By means of the use of the composition according to the invention, faster and more complete epidermization will be obtained. This will enable there to be less delay in providing the doctor with a kind of biological dressing for autografts, for example in the case of extensive burns. The invention will also enable good quality reconstituted skins for carrying out penetration or tolerance tests to be produced industrially and competitively.

Naturally, the invention comprises all means constituting technical equivalents of the means described, as well as the various combinations thereof.

We claim:

1. A method of treatment selected from the group consisting of promoting the cohesion of the cells of the epidermis, promoting keratynocite differentiation and improving the quality of hair constitution, comprising administering to zones of the skin and scalp in need thereof an effective amount of an ecdysteroid component selected from the group consisting of an ecdysteroid, a plant extract containing said ecdysteroid and an animal extract containing said ecdysteroid.

2. The method of claim 1, wherein said ecdysteroid component is formulated as a composition containing from 0.001 to 5% by weight of said ecdysteroid component relative to the total weight of the composition.

3. The method of claim 1, wherein said ecdysteroid component is present in a composition containing from 0.01 to 1% by weight of said ecdysteroid component relative to the total weight of the composition.

4. The method of claim 1, wherein said ecdysteroid component is selected from the group consisting of ecdysterone, an acylated ecdysterone, an hydroxylated ecdysterone and a deoxyecdysterone.

5. The method of claim 4, wherein said acylated ecdysterone is selected from the group consisting of an ecdysterone monoacetate and an ecdysterone multiacetate.

6. The method of claim 1, wherein said ecdysteroid component is selected from the group consisting of β-ecdysone 2-acetate, β-ecdysone 3-acetate, β-ecdysone 2,3-diacetate, β-ecdysone 2,3,22-triacetate, β-ecdysone 2,3,22,25-tetraacetate, 5-hydroxyecdysterone and 2-deoxyecdysterone.

7. The method of claim 1, wherein said extract containing said ecdysteroid is selected from the group consisting of an extract of *Achyranthes dibentata, Paris axialis, Paris fargesii, Paris dunniana, Paris vietnamensis, Paris polyphylla, Polypodium vulgare, Cyanotis arachnoidea, Ajuga decumbens, Pfaffia paniculata, Pfaffia iresinoides, Vitex glabrate, Achyranthes aspera, Sesuvium portulacastrum, Serratula sogdiana, Rhaponticum integrifolium, Rhaponticum* (or Leuzea) *carthamoides, Silene tatarica, Silene otites, Silene scabrifolia, Silene nutans, Silene brahuica, Silene traemixta, Silene dioca, Lychnis flos-cuculi, Ajuga iva, Serratula tinctoria, Cyathula officinalis, Cyathula capitata* and *Bombys mori*.

8. The method of claim 1, wherein said plant or animal extract containing said ecdysteroid is an extract of a plant or animal selected from the group consisting of *Polypodium vulgare, Ajuga decumbens, Cyanotis arachnoidea, Achyranthes bidentata* and *Rhaponticum* (or Leuzea) *carthamoides*.

9. The method of claim 1 further comprising administering in addition to said ecdysteroid component, an ajugasterone component selected from the group consisting of ajugasterone C, ajugasterone C 2-monoacetate and ajugasterone C 3-monoacetate.

10. The method of claim 1, wherein said ecdysteroid component is at least partially incorporated in liposomes.

11. The method of claim 1, further comprising administering said ecdysteroid component in combination with an active principle having a hydrating effect.

12. The method of claim 1, further comprising administering said ecdysteroid component in combination with hyaluronic acid.

13. The method of claim 1, which is a method of cosmetic treatment of a skin selected from the group consisting of a dry skin, an ichthyotic skin and a psoriatic skin.

14. The method of claim 1, which is a dermatological treatment of a skin selected from the group consisting of a dry skin, an ichthyotic skin and a psoriatic skin.

15. The method of claim 1, wherein said ecdysteroid component is at least partially included in cyclodextrine.

* * * * *